US012590059B2

(12) United States Patent
Hu et al.

(10) Patent No.: US 12,590,059 B2
(45) Date of Patent: Mar. 31, 2026

(54) PROCESS FOR THE PRODUCTION OF LEVETIRACETAM

(71) Applicant: Suzhou BrightHope Pharmatech Co., Ltd, Jiangsu Province (CN)

(72) Inventors: Songzhou Hu, Princeton, NJ (US); Lijun Deng, Hubei (CN); Wen Yu, Hubei (CN); Zhen Song, Shanghai (CN)

(73) Assignee: SUZHOU BRIGHTHOPE PHARMATECH CO., LTD, Jiangsu Province (CN)

( * ) Notice: Subject to any disclaimer, the term of this patent is extended or adjusted under 35 U.S.C. 154(b) by 460 days.

(21) Appl. No.: 18/210,330

(22) Filed: Jun. 15, 2023

(65) Prior Publication Data

US 2024/0327344 A1 Oct. 3, 2024

Related U.S. Application Data

(60) Provisional application No. 63/455,224, filed on Mar. 28, 2023.

(51) Int. Cl.
*C07D 207/27* (2006.01)

(52) U.S. Cl.
CPC ........ *C07D 207/27* (2013.01); *C07B 2200/13* (2013.01)

(58) Field of Classification Search
CPC .................................................... C07D 207/27
See application file for complete search history.

(56) References Cited

U.S. PATENT DOCUMENTS

| | | | |
|---|---|---|---|
| 4,696,942 A | 9/1987 | Gobert et al. | |
| 4,696,943 A | 9/1987 | Gobert et al. | |
| 4,837,223 A | 6/1989 | Gobert et al. | |
| 4,943,639 A | 7/1990 | Gobert et al. | |
| 6,107,492 A | 8/2000 | Futagawa et al. | |
| 6,124,473 A | 9/2000 | Cavoy et al. | |
| 6,686,477 B2 | 2/2004 | Boaz et al. | |
| 6,713,635 B2 | 3/2004 | Surtees et al. | |
| 7,122,682 B2 | 10/2006 | Ates et al. | |
| 7,563,912 B2 | 7/2009 | Ates et al. | |
| 7,902,380 B2 | 3/2011 | Li et al. | |
| 7,939,676 B2 | 5/2011 | Colli et al. | |
| 8,492,416 B2 | 7/2013 | Kenda et al. | |
| 11,085,059 B2 | 8/2021 | Xiao et al. | |
| 11,384,050 B1 * | 7/2022 | Hu | C07C 253/30 |
| 11,498,897 B2 | 11/2022 | Chen et al. | |
| 2007/0142647 A1 | 6/2007 | Ates et al. | |
| 2008/0146819 A1 | 6/2008 | Mandal et al. | |
| 2010/0076204 A1 | 3/2010 | Forcato et al. | |
| 2020/0172479 A1 | 6/2020 | Chen et al. | |
| 2022/0162165 A1 | 5/2022 | Liu et al. | |
| 2022/0242819 A1 | 8/2022 | Hu | |
| 2022/0324801 A1 | 10/2022 | Hu | |

FOREIGN PATENT DOCUMENTS

| | | | |
|---|---|---|---|
| CN | 101885696 | A | 11/2010 |
| CN | 101333180 | B | 5/2011 |
| CN | 101748087 | B | 11/2011 |
| CN | 102558012 | A | 7/2012 |
| CN | 102994429 | B | 5/2014 |
| CN | 103922988 | A | 7/2014 |
| CN | 106187851 | A | 12/2016 |
| CN | 106432032 | A | 2/2017 |
| CN | 107915667 | A | 4/2018 |
| CN | 106591179 | B | 7/2018 |
| CN | 108329247 | A | 7/2018 |
| CN | 108409592 | A | 8/2018 |
| CN | 108440364 | A | 8/2018 |
| CN | 108707099 | A | 10/2018 |
| CN | 108821992 | A | 11/2018 |
| CN | 109053528 | A | 12/2018 |
| CN | 109134308 | A | 1/2019 |
| CN | 109134341 | A | 1/2019 |
| CN | 109943618 | A | 6/2019 |
| CN | 110003074 | A | 7/2019 |
| CN | 110028434 | A | 7/2019 |
| CN | 110590635 | A | 12/2019 |
| CN | 110698379 | A | 1/2020 |
| CN | 111004138 | A | 4/2020 |
| CN | 113861090 | A | 12/2021 |
| CN | 114702426 | A | 7/2022 |
| CN | 115260075 | A | 11/2022 |
| GB | 1309692 | A | 3/1973 |
| WO | 2004083180 | A1 | 9/2004 |
| WO | 2005023763 | A1 | 3/2005 |
| WO | 2007080470 | A1 | 7/2007 |
| WO | 2008012268 | A1 | 1/2008 |
| WO | 2009057137 | A1 | 5/2009 |
| WO | 2019028666 | A1 | 2/2019 |
| WO | 2019028669 | A1 | 2/2019 |
| WO | 2019028671 | A1 | 2/2019 |
| WO | 2019029598 | A1 | 2/2019 |
| WO | 2020216146 | A1 | 10/2020 |
| WO | 2022001649 | A1 | 1/2022 |
| WO | 2022169747 | A1 | 8/2022 |

OTHER PUBLICATIONS

International Search Report with written opinion issued by the International Searching Authority for International Patent Application No. PCT/US24/21543, mailed on Jul. 5, 2024.

F.W. Jones, "Hydrolysis of Peptide Bonds Participation of a Carboxyl Group In Amide Hydrolysis", Doctoral Thesis, University of Canterbury, 1967, pp. 1-141, Christchurch, New Zealand.

* cited by examiner

*Primary Examiner* — Kamal A Saeed
(74) *Attorney, Agent, or Firm* — Myers Wolin, LLC

(57) ABSTRACT

There is disclosed a process for the production of levetiracetam by crystallizing levetiracetam in an aqueous solution, optionally in the presence of a water-soluble solvent. The product of levetiracetam contains no residual organic solvent.

13 Claims, 3 Drawing Sheets

PROCESS FOR THE PRODUCTION OF LEVETIRACETAM

CROSS REFERENCE

This application claims the benefit under 35 U.S.C. § 119(e) from U.S. Provisional Application No. 63/455,224, filed on Mar. 28, 2023, the contents of which are incorporated by reference herein.

FIELD OF THE INVENTION

This invention relates to a process for the production of levetiracetam; more particularly, it relates to a process for the production, isolation, and purification of levetiracetam in an aqueous solution.

BACKGROUND OF THE INVENTION

Levetiracetam is the S-enantiomer of etiracetam in a class of medications called anticonvulsants. It is used in combination with other medications to treat certain type of seizures in adults and children with epilepsy. Levetiracetam has the following structure:

(I)

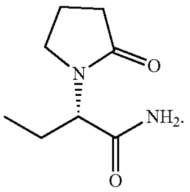

Although numerous methods have been developed for preparing levetiracetam, it is commercially produced by one of the two methods first disclosed in GB 1309692 and U.S. Pat. No. 4,696,943. In the first method, 2-pyrrolidinone and alkyl 2-halobutyrate are used as the starting materials in a process according to the following reaction scheme:

Scheme 1

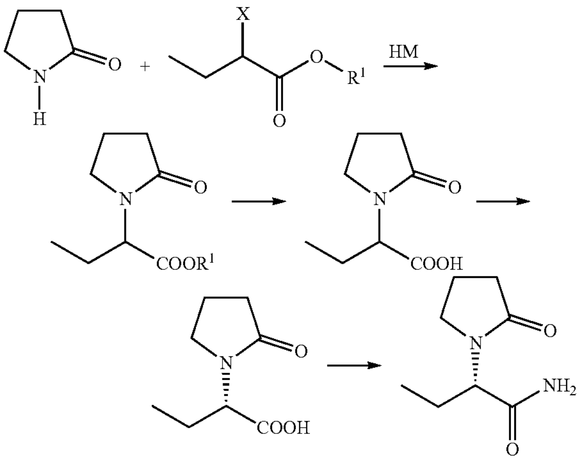

(I)

wherein X is halogen, HM is metal hydride, and $R^1$ is an alkyl group.

In the second method, L-2-aminobutanamide hydrochloride and alkyl 4-halobutyrate or 4-halobutyryl halide are used as the starting materials in a process according to the following reaction scheme:

Scheme 2

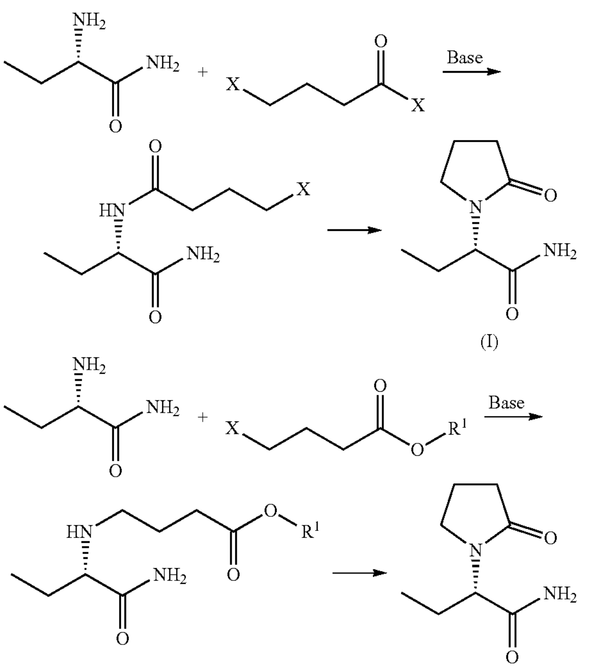

(I)

(I)

wherein X is halogen, $R^1$ is an alkyl group, and the base is an organic or inorganic base such as triethylamine or sodium carbonate.

There are inherent disadvantages in these two methods for the production of levetiracetam. In the process according to the first method, the metal hydride, which is required to deprotonate 2-pyrrolidinone, is dangerous to handle on a large scale and presents serious safety issues for the manufacturing plant. In addition, the alkyl 2-halobutyrate ester is not only unavailable commercially but also extremely obnoxious, posing environmental and occupational problems.

In the process according to the second method, just like the alkyl 2-halobutyate in the process of the first method, alkyl 4-halobutyrate and 4-halobutyryl halide are also extremely obnoxious, posing the same environmental and occupational problems. In addition, L-2-aminobutanamide hydrochloride is specifically produced for levetiracetam and as a result is costly. L-2-aminobutanamide hydrochloride is produced either from racemic 2-aminobutanamide by optical resolution or from L-2-aminobutyric acid, which is not one of the naturally occurring L-amino acids, but specifically produced for the purpose. Although there have been intensive efforts to improve the process for producing L-2-aminobutanamide hydrochloride and L-2-aminobutyric acid, they are still costly. In addition, during the cyclization under strongly basic condition, the product of levetiracetam is partially racemized or hydrolyzed.

Levetiracetam is known to have high solubility in water at about 100 g/100 mL water. Therefore, the production of levetiracetam has been carried out in an organic solvent, such as dichloromethane, toluene, etc. Similarly, the purification of levetiracetam has also been carried out in an organic solvent, such as acetone or ethyl acetate. However, the use of organic solvents in large scale production is not desirable.

U.S. Pat. No. 11,384,050 discloses an efficient process for the production of levetiracetam that has ameliorated many of the disadvantages of the known processes. But the production and purification of levetiracetam are still carried out in organic solvents.

It is an object of the present invention to overcome these inherent disadvantages in the processes for preparing levetiracetam. It is another object of the present invention to disclose a process for the production and purification of levetiracetam in an aqueous solution. The process according to the present invention can yield a product of levetiracetam that is devoid of residual organic solvent.

SUMMARY OF THE INVENTION

The present invention relates to a process for the production of levetiracetam from (S)-acid of formula (II) in aqueous solution. The present invention further discloses a process for the purification of levetiracetam in water. The process according to the present invention can produce a product of levetiracetam that is devoid of residual organic solvent.

DETAILED DESCRIPTION OF THE INVENTION

The present invention relates to a process for the production and purification of levetiracetam in an aqueous solution. The invention was accomplished by a surprising and unexpected discovery that levetiracetam can be crystallized from water and that levetiracetam can be separated from reaction impurities in water.

Figure 1:
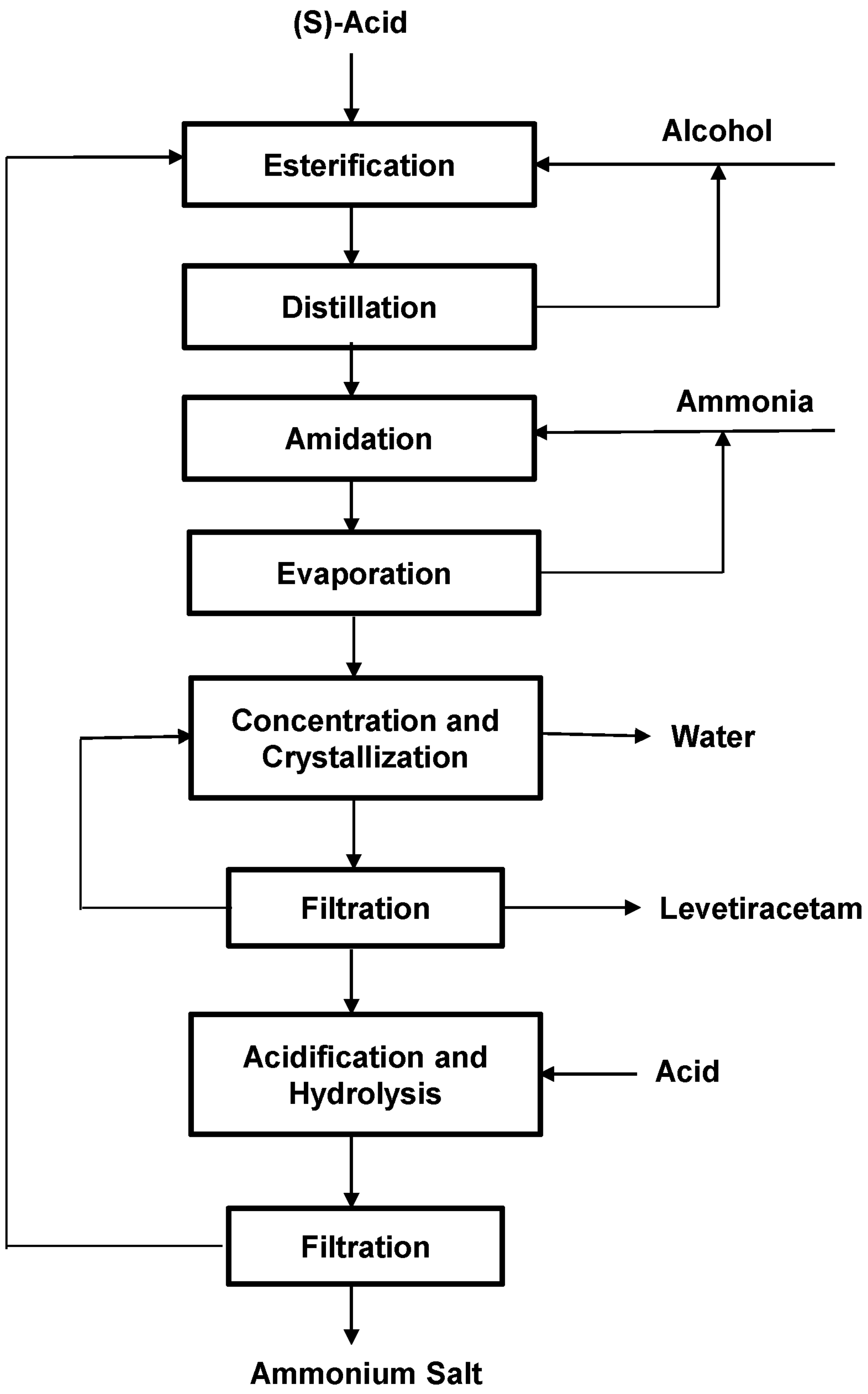
FIG. 1 illustrates one embodiment of a schematic flowchart for the production of levetiracetam from the (S)-acid of formula (II).

FIG. 1 illustrates one embodiment of the process according to the present invention. The process according to the present invention can be started from an esterification of the (S)-acid of formula (II) with an alcohol, optionally in the presence of a catalyst, followed by an amidation reaction of the ester of formula (III) in an aqueous solution of ammonium hydroxide according to the following reactions:

Scheme 3

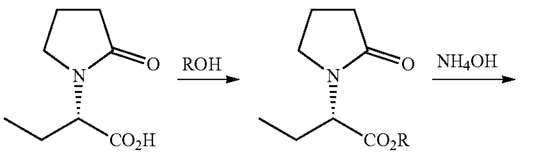

(II) (III)

-continued

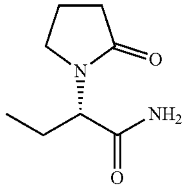

(I)

wherein R is a lower alkyl group of $C_1$-$C_8$.

The (S)-acid of formula (II) can be obtained from any source or from any process. Preferably, it is obtained by optical resolution from a racemic acid. The optically purity of the (S)-acid is at least 85%, preferably more than 90%, more preferably more than 95%, most preferably more than 97%.

A suitable alcohol can be selected from the group consisting of methanol, ethanol, propanol, isopropanol, butanol, isobutanol, cyclopropyl methanol, benzyl alcohol, and a mixture thereof.

A suitable catalyst for the esterification can be selected from the group consisting of sulfuric acid, hydrochloric acid, hydrobromic acid, thionyl chloride, phosgene, diphosgene, triphosgene, phosphorus chloride, phosphoryl chloride, alkylsulfonic acid, arylsulfonic acid, cation ion exchange resin, and a mixture thereof.

After the (S)-acid is converted to the (S)-ester of formula (III), the catalyst is removed from the reaction solution. For an acidic catalyst, it can be neutralized with a base, such as alkali hydroxide, alkali carbonate, alkali bicarbonate, ammonium hydroxide, ammonium bicarbonate, and ammonium carbonate. For a solid catalyst such as cation exchange resin, it can be removed by filtration. Excess alcohol is then removed by distillation to yield a solution of the (S)-ester of formula (III). The ester is mixed with an aqueous solution of ammonia or ammonium hydroxide to undergo an amidation reaction of the (S)-ester. The amidation reaction is preferably carried out in the presence of excess ammonia. The molar ratio of ammonia to the (S)-ester is at least 1:1, preferably 2:1; more preferably, 5:1; and most preferably, 8:1.

After the (S)-ester of formula (III) is converted to levetiracetam of formula (I), excess ammonia is removed from the reaction solution by evaporation to obtain an aqueous solution of levetiracetam. The excess ammonia may be recovered and recycled to the amidation stage.

The aqueous solution of levetiracetam may be then concentrated by methods known to one of ordinary skill in the art. It has been surprising and unexpected to find that levetiracetam can be crystallized from this concentrated aqueous solution without using any organic solvent. The crystalline levetiracetam can be isolated by a solid-liquid separation method, such as filtration, centrifuge, or press filtration to yield a mother liquor solution. The crystalline levetiracetam separated from the aqueous mother liquor solution is substantially free from reaction byproducts. It is more surprising and unexpected to find that crystalline solid of levetiracetam isolated from an aqueous solution contains less than 15% of water, preferably less than 10%, more preferably less than 5% of water on the basis of dry weight of levetiracetam.

It is also possible to add a water-soluble solvent to an aqueous solution of levetiracetam to crystallize levetiracetam. A suitable water-soluble solvent can be selected from the group consisting of methanol, ethanol, n-propanol, isopropanol, methoxyethanol, ethoxyethanol, ethylene glycol, propylene glycol, dimethyl formamide, dimethyl acetamide, dimethyl sulfoxide, tetrahydrofuran, dioxane, and a mixture thereof.

The mother liquor solution can be repetitively concentrated to crystallize levetiracetam, until impurities accumulate to such an extent that levetiracetam no longer crystallizes. Analysis of the final mother liquor revealed that the mother liquor solution contains, in addition to residual levetiracetam, the following byproducts or impurities:

(IV)

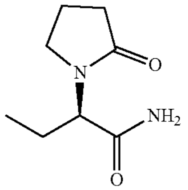

(V)

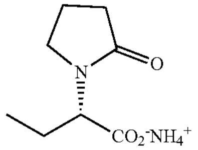

(VI)

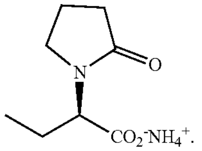

It has been found that these byproducts or impurities can be converted to starting material for the production of levetiracetam in the process according to the present invention. In particular, it is advantageous to treat the mother liquor solution with an acid to convert the ammonium salt to an acid of formula (II) and the amide into an acid of formula (II) and ammonium salt. The acid of formula (II) can be crystallized from the solution and separated by a solid-liquid separation.

A suitable acid for the conversion of the ammonium salt and residual levetiracetam to an acid of formula (II) can be selected from the group consisting of sulfuric acid, hydrochloric acid, hydrobromic acid, nitric acid, phosphoric acid, alkyl sulfonic acid, aryl sulfonic acid, and a mixture thereof. Preferably, the acid is sulfuric acid or hydrochloric acid.

If the acid of formula (II) has an optical purity of at least 90%, it can be returned to the esterification stage. Otherwise, the acid can be subject to optical resolution by methods, known to one skilled in the art, to yield substantially pure (S)-acid. The (S)-acid is then used to produce levetiracetam in the process according to the present invention.

Figure 2:
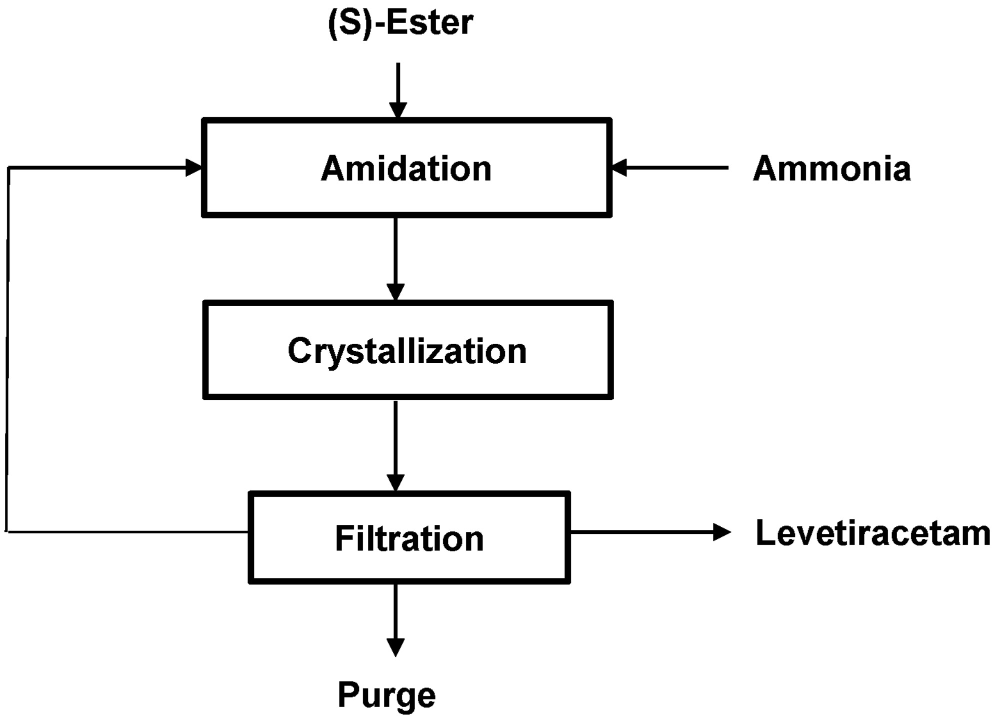
FIG. 2 illustrates one embodiment of a schematic flowchart for the production of levetiracetam from the (S)-ester of formula (III).

FIG. 2 illustrates another embodiment of the process according to the present invention, wherein a (S)-ester of formula (III) is added to an aqueous solution of ammonia, optionally in the presence of a water-soluble solvent, to undergo an amidation reaction. A suitable water-soluble solvent can be selected from the group consisting of methanol, ethanol, n-propanol, isopropanol, methoxyethanol, ethoxyethanol, ethylene glycol, propylene glycol, dimethyl formamide, dimethyl acetamide, dimethyl sulfoxide, tetrahydrofuran, dioxane, and a mixture thereof.

The product of levetiracetam is found to precipitate from the reaction solution. After the solid levetiracetam is separated, to the mother liquor solution is added additional ammonia and the (S)-ester of formula (III) to undergo further reaction. The cyclic process according this embodiment of the process is particularly advantageous, as no recycling of ammonia by distillation is needed.

In order to produce levetiracetam of pharmaceutical grade, it is necessary to further purify a crude product of levetiracetam. It has been surprising and unexpected to find that levetiracetam of pharmaceutical grade can be obtained by recrystallization from an aqueous solution, optionally in the presence of a water-soluble solvent.

A suitable water-soluble solvent can be selected from the group consisting of methanol, ethanol, n-propanol, isopropanol, methoxyethanol, ethoxyethanol, ethylene glycol, propylene glycol, dimethyl formamide, dimethyl acetamide, dimethyl sulfoxide, tetrahydrofuran, dioxane, and a mixture thereof.

Figure 3:
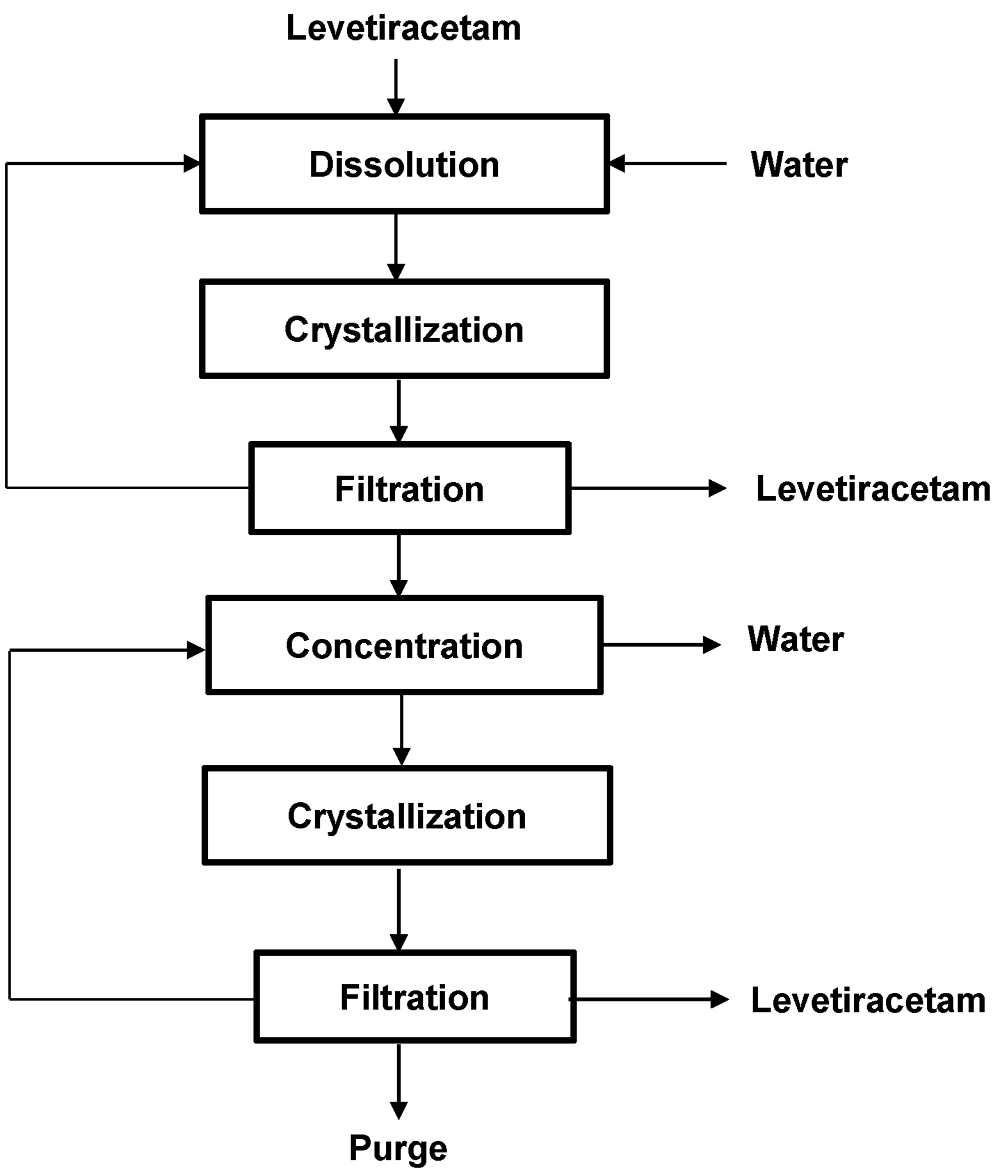
FIG. 3 illustrates one embodiment of a schematic flowchart for the purification of levetiracetam.

FIG. 3 illustrates one embodiment of the process for the purification of levetiracetam according to the present invention. A suitable crude levetiracetam can be obtained from any source or by any process. For example, crude levetiracetam can be obtained by processes illustrated in Scheme 1 or Scheme 2. Preferably, a crude levetiracetam is produced by an amidation reaction of a (S)-ester of formula (III) in the presence of excess ammonium hydroxide as shown in Scheme 3.

After crude levetiracetam is dissolved in water to obtain a saturated solution at a temperature higher than crystallization temperature, the solution is optionally treated with decoloring charcoal to remove any coloration material. After cooling, crystalline levetiracetam is obtained and can be separated by a solid-liquid separation method. The mother liquor solution can be returned to dissolve additional crude levetiracetam for purification.

Optionally, the mother liquor solution can be repetitively concentrated to crystallize levetiracetam until impurities start to accumulate in the mother liquor solution to such a high concentration that they adversely affect the purities of levetiracetam. Then, the mother liquor solution is purged from the cyclic process.

The purged mother liquor solution contains residual levetiracetam and impurities. It has been found that this purged mother liquor solution can be treated with an acid to convert residual levetiracetam to the (S)-acid of formula (II) to recover a valuable intermediate.

It is surprising and unexpected to discover that crystalline solid levetiracetam isolated from an aqueous solution contains less than 15% of water, preferably less than 10%, more preferably less than 5% of water on the basis of dry weight of levetiracetam.

It is further noted that the purification process according to the present invention can yield a product of levetiracetam that contains no residual organic solvent, an advantageous quality not attainable by prior art processes.

The purification of levetiracetam in water in the process according to the present invention can also be carried out in an aqueous solution containing water-soluble solvents. A suitable solvent can be selected from the group consisting of methanol, ethanol, n-propanol, isopropanol, methoxyethanol, ethoxyethanol, tetrahydrofuran, dioxane, acetonitrile, propionitrile, 3-methoxypropionitrile, dimethylformamide, diethylacetamide, dimethysulfoxide, tert-butanol, and a mixture thereof.

The process according to the present invention can produce levetiracetam in a molar yield of at least 80%, preferably, more than 85%, more preferably, more than 90%, most preferably, more than 95%, on the basis of the (S)-acid of formula (II).

The process according to the present invention is particularly advantageous in that the product of levetiracetam does not contain any residual organic solvent, if the production and purification are carried out in water.

The process according to the present invention can be carried out discontinuously, semi-continuously, or continuously.

EXAMPLES

The following examples will illustrate the practice of this invention but are not intended to limit its scope.

Example 1

To a flask were added 520 g of the methyl ester of formula (III) and 880 g of 25% ammonia. The solution was stirred at 10° C. for 14 hours. HPLC analysis showed that the solution contained 88.5% of levetiracetam and 11.5% of the (S)-acid of formula (II) as products. The optical purity of levetiracetam in the solution was 95.1%. The starting material, the methyl ester of formula (III) was not detected. The solution was concentrated under vacuum to 740 g and cooled to 10° C. to crystallize levetiracetam, which was filtered and washed with 100 g of cold water. After drying, 181 g of a white crystalline product of levetiracetam was obtained with a chemical purity of 99.75% and optical purity of 99.6%.

The mother liquor was concentrated under vacuum to 397 g and cooled to 10° C. to crystallize levetiracetam. The crystalline suspension was filtered and washed with 50 g of cold water. After drying, 80.7 g of a white crystalline product of levetiracetam was obtained with a chemical purity of 99.6% and optical purity of 93.8%.

80.7 g of the crude product of an optical purity of 93.8% was recrystallized from 60 g of water to yield 30.0 g of white crystalline levetiracetam with a chemical purity of 99.8% and an optical purity of 99.0%.

Example 2

To a flask were added 285 mL of methanol, 50 g of the (S)-acid of formula (II), and 1.5 g of sulfuric acid. The solution was refluxed at 67° C. for 3 hours to obtain the methyl ester of formula (III) in a yield of 97.9%. After the solution was cooled to 30° C., the sulfuric acid was neutralized with 2.0 g of ammonium bicarbonate to a pH of 6-7. The neutralized solution was further cooled to 5° C., to which was added 95.5 g of 26% ammonium hydroxide. The solution was stirred at 5° C. for 14 hours to obtain levetiracetam in a yield of 86.0%. The (S)-acid was obtained in a yield of 13.7%. 0.3% of the methyl ester remained unchanged.

Example 3

To a flask were added 93.8 g of the methyl ester of formula (III) of a purity of 93.0% and 103 g of 25% ammonium hydroxide. The solution was stirred at 5° C. for 18 hours to form a massive crystalline suspension, which was filtered and dried to obtain 48.6 g of levetiracetam, which had a chemical purity of 98.2% and an optical purity of 100%.

To the mother liquor solution were added 93.8 g of the methyl ester of formula (III) and 50 g of 25% ammonium hydroxide. The solution was stirred at 5° C. for 18 hours to form a massive crystalline suspension, which was filtered and dried to obtain 44.5 g of levetiracetam, which had a chemical purity of 99.2% and an optical purity of 99.7%.

Example 4

To a flask were added 70 mL of deionized water and 100 g of a crude product of levetiracetam with a chemical purity of 90.3% and an optical purity of 98.04%. The solid suspension was warmed up to 40° C. to obtain a clear solution, which was slowly cooled to 10° C. to crystallize levetiracetam. The crystalline suspension was filtered to obtain 18.0 g of levetiracetam after drying. The product had a chemical purity of 99.98% and an optical purity of 100%.

It will be understood that the foregoing examples, explanation, and drawings are for illustrative purposes only and that in view of the instant disclosure various modifications of the present invention will be self-evident to those skilled in the art. Such modifications are to be included within the spirit and purview of this application and the scope of the appended claims.

What is claimed is:

1. A process for the production of (S)-α-ethyl-2-oxo-1-pyrrolidineacetamide of formula (I),

I

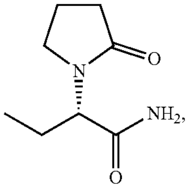

comprising: (a) reacting a (S)-ester of formula (III), (III)

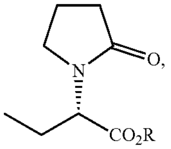

wherein R is an alkyl group of $C_1$-$C_8$, with an aqueous solution of ammonia or ammonium hydroxide, to form (S)-a-ethyl-2-oxo-1-pyrrolidineacetamide of formula (I); (b) crystallizing the (S)-a-ethyl-2-oxo-1-pyrrolidineacetamide of formula (I) of step (a) in the aqueous solution; and (c) isolating the (S)-a-ethyl-2-oxo-1-pyrrolidineacetamide of formula (I) of step (b);

and wherein the(S)-ester of formula (III), (III)

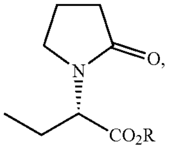

is prepared by a process comprising the steps of: (1) reacting the (S)-acid of formula (II), (II)

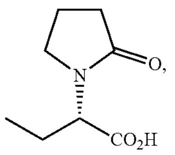

with an excess alcohol of ROH in the presence of a catalyst to form a (S)-ester of formula (III) and (2) removing the excess alcohol to obtain a solution of the (S)-ester of formula (III).

2. The process according to claim 1, wherein the (S)-α-ethyl-2-oxo-1-pyrrolidineacetamide of formula (I) is crystallized from the aqueous solution by removing excess ammonia and concentrating the aqueous solution.

3. The process according to claim 1, wherein the product of (S)-α-ethyl-2-oxo-1-pyrrolidineacetamide does not contain residual organic solvent.

4. The process according to claim 1, wherein the reaction of the (S)-ester of formula (III) with the ammonia in aqueous solution is carried out in the presence of a water-soluble organic solvent.

5. The process according to claim 4, wherein the water-soluble organic solvent is selected from the group consisting of methanol, ethanol, n-propanol, isopropanol, methoxyethanol, ethoxyethanol, tetrahydrofuran, dioxane, acetonitrile, propionitrile, 3-methoxypropionitrile, dimethylformamide, diethylacetamide, dimethysulfoxide, tert-butanol, and a mixture thereof.

6. The process according to claim 1, wherein the alcohol is selected from the group consisting of methanol, ethanol, propanol, isopropanol, butanol, isobutanol, cyclopropyl methanol, benzyl alcohol, and a mixture thereof.

7. The process according to claim 1, wherein the catalyst is selected from the group consisting of sulfuric acid, hydrochloric acid, hydrobromic acid, thionyl chloride, phosgene, diphosgene, triphosgene, phosphorus chloride, phosphoryl chloride, alkylsulfonic acid, arylsulfonic acid, cation ion exchange resin, and a mixture thereof.

8. The process according to claim 1, wherein the catalyst is removed from the reaction solution by neutralization or by filtration.

9. A process for the production of (S)-α-ethyl-2-oxo-1-pyrrolidineacetamide of formula (I), (I)

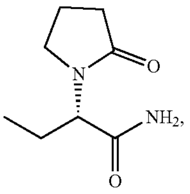

comprising:

(a) dissolving a crude product of (S)-α-ethyl-2-oxo-1-pyrrolidineacetamide of formula (I) in water, and optionally treating the solution with decolorizing charcoal;

(b) cooling the solution of step (a) to crystallize the (S)-α-ethyl-2-oxo-1-pyrrolidineacetamide of formula (I); and (c) isolating the (S)-α-ethyl-2-oxo-1-pyrrolidineacetamide of formula (I).

10. The process according to claim 9, wherein the product of (S)-α-ethyl-2-oxo-1-pyrrolidineacetamide of formula (I) contains no residual organic solvent.

11. The process according to claim 9, wherein the wet cake of (S)-α-ethyl-2-oxo-1-pyrrolidineacetamide of formula (I) contains less than 10% of water.

12. The process according to claim 9, wherein the crude product of (S)-α-ethyl-2-oxo-1-pyrrolidineacetamide of formula (I) is produced from L-2-aminobutanamide or its salt of formula

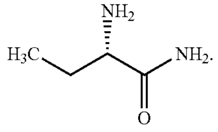

13. The process according to claim 9, wherein the crude product of (S)-α-ethyl-2-oxo-1-pyrrolidineacetamide of formula (I) is produced from L-2-aminobutanamide is produced from (S)-acid of formula (II)

(II)

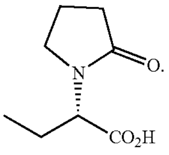

* * * * *